US012359146B2

(12) United States Patent
Du

(10) Patent No.: US 12,359,146 B2
(45) Date of Patent: Jul. 15, 2025

(54) PERSONAL CLEANSING COMPOSITION COMPRISING A MIXTURE OF TWO POLYGLYCEROL FATTY ACID ESTERS AND A SUGAR FATTY ACID ESTER

(71) Applicant: Merry Plus Corporation, Tokyo (JP)

(72) Inventor: Yao Du, Tokyo (JP)

(73) Assignee: Merry Plus Corporation, Tokyo (JP)

( * ) Notice: Subject to any disclaimer, the term of this patent is extended or adjusted under 35 U.S.C. 154(b) by 488 days.

(21) Appl. No.: 18/056,756

(22) Filed: Nov. 18, 2022

(65) Prior Publication Data
US 2023/0081952 A1 Mar. 16, 2023

Related U.S. Application Data

(63) Continuation of application No. PCT/JP2021/022300, filed on Jun. 11, 2021.

(30) Foreign Application Priority Data

Jun. 12, 2020 (JP) .................. 2020-101968
Jan. 7, 2021 (JP) .................. 2021-001168

(51) Int. Cl.
C11D 1/83 (2006.01)
C11D 1/46 (2006.01)
C11D 3/20 (2006.01)
C11D 3/33 (2006.01)

(52) U.S. Cl.
CPC .............. C11D 1/46 (2013.01); C11D 3/2065 (2013.01); C11D 3/33 (2013.01)

(58) Field of Classification Search
CPC ......... C11D 1/825; C11D 1/8255; C11D 1/83; C11D 1/10; C11D 1/18; C11D 3/43; C11D 17/0017; C11D 17/0021; C11D 2111/12; C11D 3/0094
See application file for complete search history.

(56) References Cited

U.S. PATENT DOCUMENTS

| | | | | |
|---|---|---|---|---|
| 2006/0115440 A1* | 6/2006 | Arata | ..................... | A61K 31/28 424/65 |
| 2009/0214606 A1* | 8/2009 | Bujard | .................. | A01N 59/16 424/617 |
| 2010/0034893 A1* | 2/2010 | Pfluecker | ................ | A61K 8/29 424/490 |
| 2016/0317416 A1* | 11/2016 | Derrips | .................. | A61K 8/062 |
| 2018/0280261 A1* | 10/2018 | Nioh | ..................... | A61K 8/602 |
| 2019/0298639 A1* | 10/2019 | Ichinokawa | ............ | A61K 8/39 |
| 2019/0336438 A1* | 11/2019 | Nakata | ..................... | A61K 8/37 |
| 2022/0047477 A1* | 2/2022 | Maruyama | ............. | A61K 8/375 |

FOREIGN PATENT DOCUMENTS

| | | |
|---|---|---|
| EP | 2832346 A1 | 2/2015 |
| JP | 2005-068083 A | 3/2005 |
| JP | 2006-028229 A | 2/2006 |
| JP | 2006-169198 A | 6/2006 |
| JP | 2014-12656 A | 1/2014 |
| JP | 2014-122198 A | 7/2014 |
| JP | 2018-016613 A | 2/2018 |
| JP | 2018-095560 A | 6/2018 |
| JP | 2020-090469 A | 6/2020 |
| JP | 6945256 B | 10/2021 |

OTHER PUBLICATIONS

International Search Report from International Application No. PCT/JP2021/022300 mailed Jul. 13, 2021.

* cited by examiner

Primary Examiner — Charles I Boyer
(74) Attorney, Agent, or Firm — Shih IP Law Group, PLLC.

(57) ABSTRACT

One object is to provide a cleansing composition that has excellent cleansing effect and phase inversion feeling, is readily rinsed off in the course of water washing, suppresses the oil-induced stickiness after the use, and has excellent preservation stability. There is provided a cleansing composition comprising: (A) a sugar ester of a fatty acid; (B) at least one type of an anionic surfactant selected from among amino acid surfactants and taurine surfactants; (C) at least one type of a polyglycerol fatty acid diester or a polyglycerol fatty acid triester having an HLB value of not greater than 13; (D) at least one type of a polyglycerol fatty acid monoester having an HLB value of not smaller than 11; (B) an oil that has a liquid form or a paste (non-solid) form at ordinary temperature; (F) a polyol; and (G) water.

9 Claims, No Drawings

PERSONAL CLEANSING COMPOSITION COMPRISING A MIXTURE OF TWO POLYGLYCEROL FATTY ACID ESTERS AND A SUGAR FATTY ACID ESTER

TECHNICAL FIELD

The present disclosure relates to a cleansing composition mainly used for the skin.

BACKGROUND

Cleansing cosmetic preparations (cleansing compositions) formulated to include an oil agent and a surface active agent as primary components have generally been used to remove oily spots such as the remaining cosmetic preparations for the makeup or spots on the skin. Such cleansing cosmetic preparations are generally used to be applied on the skin and washed out with water or wiped out with tissue paper or the like.

Various types of cleansing cosmetic preparations are commercially available. Among them, oil-in-water type cleaning cosmetic preparations have the good feeling of use but have a disadvantage of low cleansing effect. Water-in-oil type or oil-based cleaning cosmetic preparations, on the other hand, have high cleansing effect but still have a room for improving the feeling of use, for example, the stickiness and the non-easiness of rinse-off with water.

Emulsion-type cleansing cosmetic preparations applying D-phase emulsification have been developed recently, in order to satisfy both the cleaning effect and the good feeling of use. The emulsion-type cleansing cosmetic preparations are characterized by the low friction in the course of rubbing and massaging the skin, the softness to the skin, and the high affinity to water to give the fresh feeling after rinse-off with water.

The emulsion-type cleansing product applying the D-phase emulsification is generally prepared by adding an oil to a phase formed by mixing a surface active agent, a polyol, and water and thus contains a large amount of oil that contributes to efficiently remove the makeup. For example, a disclosed emulsion-type skin external agent includes 60% to 80% by mass of an oil agent, 1% to 2% by mass of a glyceryl polyoxyethylene fatty acid ester, and 0.5 to 2% by mass of a fatty acid (refer to, for example, Patent Literature 1). A disclosed cleansing composition includes a sugar ester of a fatty acid, an anionic surfactant, a polyoxyalkylene polyol fatty acid ester having an HLB value of not greater than 12, an oil, a polyol and water (refer to, for example, Patent Literature 2). As a general oil-in-water type cleansing product that is not a D-phase emulsion type, a disclosed cleansing cosmetic preparation includes two or more different types of polyglycerol fatty acid esters having HLB values of 10 to 17 and also includes at least one type of or multiple types of anionic surfactants (refer to, for example, Patent Literature 3).

CITATION LIST

Patent Literature

Patent Literature 1: JP 2006-169198A
Patent Literature 2: JP 2018-95560A
Patent Literature 3: JP 2018-16613A

SUMMARY

Technical Problem

The cleansing composition is, however, required to have not only the cleansing effect and the satisfactory feeling of use, but additional values, such as the preservation stability at high temperatures and at low temperatures, the pleasant feeling of the skin after the use, the gentleness on the skin, and the luxurious (transparency) looking. It is accordingly apparent that there is still a room for further improvement.

The skin external preparation described in Patent Literature 1 includes the fatty acid and requires neutralization at the end of the manufacturing process. This process is more complicated than the conventional D-phase emulsification. Furthermore, the skin external preparation still has problems of the phase inversion feeling, which is an important indication of the feeling of use and is a feeling of increasing the smoothness of the finger by spreading the agent on the skin, and the easiness of rinse-off. Furthermore, the cleansing composition described in Patent Literature 2 has the good phase inversion feeling but still has problems of the easiness of rinse-off with water during use and the stickiness after the use (the feeling of oil film persistency on the dried skin).

In many cases, actually sold cosmetic preparations include multiple different types of polyglycerol fatty acid esters as an emulsifier and a surface active agent as described in Patent Literature 3. Any of such conventional cleansing agents, however, still has a problem of the feeling of oil film persistence caused by a large content of oil or, on the contrary, has a problem of the poor cleansing power caused by a small content of oil. For example, Patent Literature 3 requires, for example, an (acrylate/alkyl acrylate) cross-linked polymer having an alkyl group of 10 to 30 carbon atoms and a higher alcohol of 12 to 20 carbon atoms to be additionally mixed in addition to the polyglycerol fatty acid esters and the anionic surfactant, with a view to obtaining a stable composition. It is accordingly difficult that the cosmetic preparation has stably contain not lower than 50% of the oil in its inner phase, which is expected to be increased for the purpose of improving the low cleansing power. There is still a room for improving the cleansing power against the makeup of the high adhesiveness, such as a waterproof mascara.

By taking into account the problem described above, an object of the present disclosure is to provide a cleansing composition that has a large content of oil but minimizes the amount of surface active agents, so as to have excellent cleansing effect and phase inversion feeling, to be readily rinsed off in the course of water washing, to suppress the feeling of oil film persistence of the skin after the use (the stickiness after the use), and to have excellent preservation stability.

Solution to Problem

In order to achieve the above object, according to one aspect of the invention, there is provided a cleansing composition, comprising components (A) to (G): (A) a sugar ester of a fatty acid; (B) at least one type of an anionic surfactant selected from among amino acid surfactants and taurine surfactants; (C) at least one type of a polyglycerol fatty acid diester or a polyglycerol fatty acid triester having an HLB value of not greater than 13; (D) at least one type of a polyglycerol fatty acid monoester having an HLB value of not smaller than 11; (E) an oil that has a liquid form or a paste (non-solid) form at ordinary temperature; (F) a polyol; and (G) water.

A ratio (E)/((C)+(D)) of a mass of the component (E) to a total mass of the component (C) and the component (D) is 10 to 100. A ratio (C)/(D) of a mass of the component (C) to a mass of the component (D) is 0.1 to 10. A ratio ((C)+(D))/(A) of the total mass of the component (C) and the component (D) to a mass of the component (A) is 0.02 to 4.

In the cleansing composition of the above aspect, it is preferable that the component (E) is in a range of 40% by mass to 90% by mass relative to a total mass of the cleansing composition.

In the cleansing composition of the above aspect, it is preferable that the component (C) preferably has the HLB value of 7 to 13, and the component (D) preferably has the HLB value of 11 to 16.

In the cleansing composition of the above aspect, it is preferable that the component (C) is polyglyceryl-6 dicaprate, and the component (D) is polyglyceryl-10 laurate.

In the cleansing composition of the above aspect, it is preferable that the component (C) is at least one selected from among polyglyceryl-6 dicaprate, polyglyceryl-10 dimyristate, polyglyceryl-5 dilaurate, polyglyceryl-10 distearate, polyglyceryl-2 sesquioleate, polyglyceryl-10 dioleate, polyglyceryl-10 distearate, polyglyceryl-10 diisostearate, polyglyceryl-5 dioleate, and polyglyceryl-10 trilaurate.

In the cleansing composition of the above aspect, it is preferable that the component (D) is at least one selected from among polyglyceryl-10 laurate, polyglyceryl-4 laurate, polyglyceryl-6 caprate, polyglyceryl-10 caprate, polyglyceryl-5 myristate, polyglyceryl-5 stearate, polyglyceryl-5 caprate, polyglyceryl-10 myristate, polyglyceryl-10 oleate, polyglyceryl-10 stearate, polyglyceryl-5 laurate, polyglyceryl-5 oleate, polyglyceryl-10 laurate, polyglyceryl-10 myristate, polyglyceryl-10 stearate, polyglyceryl-10 isostearate, and polyglyceryl-6 oleate.

In the cleaning composition of the above aspect, it is preferable that the component (C) is polyglyceryl-6 dicaprate and that the component (D) is polyglyceryl-4 laurate. In the cleaning composition of the above aspect, it is preferable that the component (C) is polyglyceryl-6 dicaprate and that the component (D) is polyglyceryl-6 caprate.

In the cleaning composition of the above aspect, it is preferable that the component (C) is polyglyceryl-10 trilaurate and that the component (D) is polyglyceryl-10 laurate. In the cleaning composition of the above aspect, it is preferable that the component (C) is polyglyceryl-10 trilaurate and that the component (D) is polyglyceryl-4 laurate. In the cleaning composition of the above aspect, it is preferable that the component (C) is polyglyceryl-10 trilaurate and that the component (D) is polyglyceryl-6 caprate.

In the cleaning composition of the above aspect, it is preferable that the component (C) is polyglyceryl-10 dimyristate and that the component (D) is polyglyceryl-4 laurate. In the cleaning composition of the above aspect, it is preferable that the component (C) is polyglyceryl-10 dimyristate and that the component (D) is polyglyceryl-10 laurate. In the cleaning composition of the above aspect, it is preferable that the component (C) is polyglyceryl-10 dimyristate and that the component (D) is polyglyceryl-6 caprate.

In the cleaning composition of the above aspect, it is preferable that the ratio ((C)+(D))/(A) of the total mass of the component (C) and the component (D) to the mass of the component (A) is 0.1 to 2.

In the cleaning composition of the above aspect, it is preferable that the component (A) is in a range of 0.1% by mass to 5% by mass, the component (B) is in a range of 0.05% by mass to 5% by mass, the component (C) is in a range of 0.01% by mass to 5% by mass, the component (D) is in a range of 0.01% by mass to 5% by mass, the component (E) is in a range of 50% by mass to 85% by mass, the component (F) is in a range of 0.1% by mass to 15% by mass, and the component (G) is in a range of 0.1% by mass to 15% by mass to a total mass of the cleansing composition.

The cleansing composition of the above aspect is preferably a skin cleansing cosmetic preparation. It is preferable to use the cleansing composition to be directly applied on any of the face, the body, the limbs, the hair and the like, to be rubbed to spread over the spot and to be wiped out or washed out.

Advantageous Effects

According to an aspect of the present disclosure, there is provided a cleansing composition comprising: (A) a sugar ester of a fatty acid; (B) at least one type of an anionic surfactant selected from among amino acid surfactants and taurine surfactants; (C) at least one type of a polyglycerol fatty acid diester or a polyglycerol fatty acid triester having an HLB value of not greater than 13; (D) at least one type of a polyglycerol fatty acid monoester having an HLB value of not smaller than 11; (E) an oil that has a liquid form or a paste (non-solid) form at ordinary temperature; (F) a polyol; and (G) water. A ratio (E)/((C)+(D)) of a mass of the component (E) to a total mass of the component (C) and the component (D) is 10 to 100. A ratio (C)/(D) of a mass of the component (C) to a mass of the component (D) is 0.1 to 10. A ratio ((C)+(D))/(A) of the total mass of the component (C) and the component (D) to a mass of the component (A) is 0.02 to 4. This configuration causes the cleansing composition of the present disclosure to have excellent cleansing effect and phase inversion feeling, to be readily rinsed off in the course of water washing, to suppress the feeling of oil film persistence of the skin after the use (the stickiness after the use), and to have excellent preservation stability.

DESCRIPTION OF EMBODIMENTS

[Component (A): Sugar Ester of Fatty Acid]

A sugar ester of a fatty acid that is a component (A) includes at least one sugar residue and at least one fatty acid residue. The component (A) may be selected from among esters of sugars and linear and branched saturated and unsaturated fatty acids or ester mixtures. This fatty acid may be selected from among, for example, saturated C10 to C24 fatty acids, preferably from C10 to C18 fatty acids, and more preferably from C12 to C16 fatty acids. The ester may be selected from among monoesters, diesters, triesters, tetraesters, polyesters and mixtures thereof.

The component (A): the sugar ester of the fatty acid is selected from the group consisting of sucrose laurate, sucrose myristate, sucrose palmitate, sucrose stearate, sucrose behenate, sucrose oleate, sucrose tetraisostearate, sucrose hexaisostearate, sucrose hexa(oleate/palmitate/stearate) and mixtures thereof.

Examples of commercially available products include 'Hostapon CT Pate (registered trademark)' and 'Hostapon LT-SF (registered trademark)', and 'Nikkol CMT-30-T (registered trademark)', 'Nikkol SMT (registered trademark)' and 'Nikkol PMT (registered trademark)'(the latter three manufactured by Nikko Chemicals Co., Ltd.)

In terms of improving the phase inversion feeling, the feeling of use and the preservation stability, the amount of the component (A) is in a range of 0.01% by mass to 20% by mass and is preferably in a range of 0.1% by mass to 5% by mass, relative to the total mass of the cleansing composition.

[Composition (B): At Least One Type of Anionic Surfactant Selected from Among Amino Acid Surfactants and Taurine Surfactants]

An amino acid surfactant of a component (B) is an amino acid-based or an amino acid derivative-based anionic surfactant. The amino acid surfactant is typically an anionic surfactant including at least one amino moiety and at least one carboxylic acid moiety (carboxylate moiety). The amino acid surfactant may include two or more amino moieties and/or two or more carboxylic acid moieties (carboxylate moieties).

The amino acid surfactant may preferably be selected from among amino acid derivatives. More preferably, the amino acid derivative may be selected from among salts of amino acids and N-acylated amino acids or more specifically among alkali metal salts and alkaline earth metal salts of the amino acids and the N-acylated amino acids, for example, sodium salts, potassium salts, magnesium salts and calcium salts of the amino acids and the N-acylated amino acids.

The acyl group in an N-acyl moiety of the amino acid derivative may be a C1 to C30 acyl group, preferably a C6 to C28 acyl group or more preferably a C12 to 24 acyl group.

More preferably, the amino acid surfactant is selected from the group consisting of glutamates, N-acylated glutamates, aspartates, N-acylated aspartates, and salts thereof.

Examples of commercially available products include 'Acylglutamate CT-12 (registered trademark)'(manufactured by Ajinomoto Co., Inc.) and 'Asparack (registered trademark)'(manufactured by Mitsubishi Chemical Corporation).

The taurine surfactant of the component (B) is an anionic surfactant including at least one taurine moiety. The taurine surfactant is preferably acyl taurine or more preferably acyl methyl taurine (more specifically, N-acyl-N-methyl taurine).

The taurine surfactant is selected from the group consisting of taurine, caproyl taurine, lauroyl taurine, myristoyl taurine, palmitoyl taurine, stearoyl taurine, oleoyl taurine, cocoyl taurine, methyltaurine, coconut oil fatty acid methyltaurine, palm kernel oil fatty acid methyltaurine, hydrogenated palm kernel oil fatty acid methyltaurine, tallowate methyltaurine, hydrogenated tallowate methyltaurine, caproyl methyltaurine, lauroyl methyltaurine, myristoyl methyltaurine, palmitoyl methyltaurine, stearoyl methyltaurine, oleoyl methyltaurine, cocoyl methyltaurine, methyltaurine cocoyl methyltaurine, and salts thereof.

Examples of commercially available products include 'Hostapon CT Pate (registered trademark)' and 'Hostapon LT-SF (registered trademark)', (both manufactured by Clariant AG).

In terms of ensuring easy rinse-off in the process of water washing with maintaining the preservation stability and the phase inversion feeling, the amount of the component (B) is in a range of 0.001% by mass to 20% by mass, is preferably in a range of 0.01% by mass to 10% by mass and is more preferably in a range of 0.05% by mass to 5% by mass, relative to the total mass of the cleansing composition.

[Component (C): At Least One Type of Polyglycerol Fatty Acid Diester or Polyglycerol Fatty Acid Triester Having an HLB Value of not Greater than 13 or Preferably an HLB Value of 7 to 13]

Polyglycerol fatty acid esters are available to have various HLB values by changing the type of the fatty acid as the hydrophobic group or changing the degree of polymerization of glycerol as the hydrophilic group and are thus generally used as emulsifiers or surface active agents for cosmetic preparations.

According to this embodiment, the component (C) may be at least one selected from among polyglyceryl-6 dicaprate (HLB 10.2), polyglyceryl-10 dimyristate (HLB 12.3), polyglyceryl-5 dilaurate (HLB 8.5), polyglyceryl-10 distearate (HLB 11.1), polyglyceryl-2 sesquioleate (HLB 5.3), polyglyceryl-10 dioleate (HLB 11.9), polyglyceryl-10 distearate (HLB 11.1), polyglyceryl-10 diisostearate (HLB 11.1), and polyglyceryl-5 dioleate (HLB 11.9) (all manufactured by Taiyo Kagaku Co., Ltd.)

More specifically, polyglyceryl-6 dicaprate (HLB 10.2) is preferable. A commercially available product is, for example, 'SUNSOFT Q-102H-C' (manufactured by Taiyo Kagaku Co., Ltd.) This polyglyceryl-6 dicaprate is an oil-soluble component that is generally mixed as an oil content in cosmetic preparations, retains moisture in the skin and in the hair, and softens the surface of the skin and the hair. This polyglyceryl-6 dicaprate also has functions of an excellent surface active agent (emulsifying agent).

In terms of the cleansing power, the phase inversion feeling, and the feeling of oil film persistence, the amount of the component (C) is in a range of 0.001% by mass to 10% by mass and is preferably in a range of 0.01% by mass to 5% by mass, relative to the total mass of the composition.

In the description of this embodiment, HLB (Hydrophilic-Lipophilic Balance) is an index indicating the degrees of affinity of the surfactant to water and oil and is calculated by the Griffin's equation (J. Soc. Cosmet. Chem., 1,311(1949); 5,249(1953)). The HLB value of a surfactant mixture comprised of two or more different types of nonionic surfactants (hereinafter referred to as mixture HLB) is a weighted average of the HLB values of the respective nonionic surfactants on the basis of their mixing ratio and is obtained by an equation given below:

$$\text{Mixture HLB Value} = \Sigma(\text{HLB}x \times Wx)/\Sigma Wx$$

(where HLBx represents an HLB value of a surfactant X, and Wx represents a mass (g) of the surfactant X having the value of HLBx).

A polyglycerol fatty acid triester that is an ester of three fatty acids and polyglycerol may be used as the component (C), instead of the polyglycerol fatty acid diester. It is preferable that the polyglycerol fatty acid triester has a polyglyceryl moiety derived from two to ten glycerol molecules or preferably five to ten glycerol molecules. The polyglycerol fatty acid triester used in the present disclosure is a saturated or unsaturated acid triester preferably having six to eighteen carbon atoms or more preferably having ten to fourteen carbon atoms and preferably has an alkyl chain or an alkenyl chain preferably having six to eighteen carbon atoms or more preferably having ten to fourteen carbon atoms. More specifically, the polyglycerol fatty acid triester may be at least one selected from among polyglyceryl-10 trilaurate, polyglyceryl-6 trilaurate, polyglyceryl-5 trimyristate, and polyglyceryl-5 trioleate.

[Component (D): At Least One Type of Polyglycerol Fatty Acid Monoester Having an HLB Value of not Smaller than 11 or Preferably an HLB Value of 11 to 16]

The component (D) is a polyglycerol fatty acid ester having one ester bond. Examples of the component (D) include polyglyceryl-6 caprate (HLB 14.6), polyglyceryl-10 caprate (HLB 17.3), polyglyceryl-5 myristate (HLB 15.4), polyglyceryl-5 stearate (HLB 15.0), or polyglyceryl-5 caprate (HLB 13.0) (all manufactured by Taiyo Kagaku Co., Ltd.) and mixtures of these esters. Other available examples of the ester include polyglyceryl-10 myristate (HLB 16.7), polyglyceryl-10 oleate (HLB 15.9), polyglyceryl-10 stearate (HLB 17.5), polyglyceryl-5 laurate (HLB 15.8), polyglyceryl-5 oleate (HLB 14.9), polyglyceryl-10 laurate (HLB 15.5), polyglyceryl-10 myristate (HLB 15.7), polyglyceryl-10 stearate (HLB 15.1), polyglyceryl-10 isostearate (HLB 13.7) and polyglyceryl-6 oleate (HLB 11.6) (all manufactured by Taiyo Kagaku Co., Ltd.)

More specifically, polyglyceryl-10 laurate (HLB 15.5): 'SUNSOFT M-12' (manufactured by Taiyo Kagaku Co., Ltd.) as a commercially available product and polyglyceryl-4 laurate (HLB 11.0): 'TEGO CARE PL4' (manufactured by Evonik Industries) as a commercially available product are preferable.

In terms of the phase inversion feeling, the easy rinse-off, and the preservation stability, the amount of the component (D) is preferably in a range of 0.001% by mass to 10% by mass and is more preferably in a range of 0.01% by mass to 5% by mass, relative to the total mass of the composition.

[Component (E): Oil]

The component (E) is a component that is generally usable as an oil agent for a cosmetic preparation, that is not mixable with water at an arbitrary ratio and that has a liquid form or a paste (non-solid) form at ordinary temperature of 25° C. and 1 atm. The oil may be volatile or non-volatile. Examples of the component (E) include hydrocarbon oils, silicone oils, ester oils, ether oils, vegetable oils, animal oils, aliphatic alcohols and mixtures thereof. Examples of the hydrocarbon oil include hexane, undecane, dodecane, isohexadecane, isododecane, squalane, squalene, liquid paraffin, petrolatum, polydecene, hydrogenated polyisobutene, naphthalene, isoeicosane, and decene/butene copolymer. Examples of the silicone oil include dimethylpolysiloxane, methyl phenyl polysiloxane, and cyclohexasiloxane. Examples of the ester oil include ethyl palmitate, ethyl hexyl palmitate, dicaprylyl carbonate, isopropyl lauroyl sarcosinate, isononyl isononanoate, cetyl octanoate, isodecyl neopentanoate, myristyl propionate, 2-ethylhexyl caprylate/caprate, isopropyl myristate, isostearyl palmitate, ethyl laurate, diethyl sebacate, diisopropyl adipate, and glyceryl tricaprate/tricaprylate. An example of the ether oil is dicaprylyl ether. Examples of the vegetable oil include linseed oil, camelia oil, olive oil, safflower oil, jojoba oil, sunflower oil, almond oil, macadamia nut oil, corn oil, olive oil, avocado oil, sesame oil, soybean oil and peanut oil. Examples of the animal oil include egg yolk oil, beef tallow, lard, mutton tallow, mink oil, shark liver oil, and lanolin. Examples of the aliphatic alcohol include octanol, lauryl alcohol, octyl dodecanol, hexyl decanol, and oleyl alcohol. The oils (synthetic oils and nature-derived oils) usable for the cleansing cosmetics have already been disclosed in a lot of documents (for example, Patent Literature 1 and Patent Literature 2). Any of these known oils is naturally applicable to the oil of the component (E) according to the embodiment.

In terms of the cleansing effects, the phase inversion feeling (easy spread on the skin) and easy rinse-off in the process of water washing, the amount of the component (E) is in a range of 40% by mass to 90% by mass and is preferably in a range of 50% by mass to 85% by mass, relative to the total mass of the composition.

[Component (F): Polyol]

The polyol of the component (F) is a polyalcohol and is an aliphatic compound having two or more hydroxy groups (OH groups). The polyol having two or more hydroxy groups is called glycol or diol. Typical examples of the glycol are ethylene glycol, propylene glycol and tetramethylene glycol. Other examples of the glycol include diethylene glycol and dipropylene glycol that are ethers of ethylene glycol and of propylene glycol, as well as polyethylene glycol. A typical example of the polyol having three hydroxy groups is glycerol (glycerin), and a typical example of the polyol having four hydroxy groups is pentaerythritol.

The polyol of the component (F) may be a C2 to C12 polyol or preferably a C2 to C9 polyol including at least two hydroxy groups or preferably two to five hydroxy groups.

The polyol may be a natural polyol or a synthetic polyol. The polyol may have a linear, branched or cyclic molecular structure.

The polyol may be selected from among glycerol or glycerin and its derivatives and glycols and their derivatives. The polyol may be selected from the group consisting of glycerol, diglycerol, polyglycerol, ethylene glycol, diethylene glycol, propylene glycol, dipropylene glycol, butylene glycol, pentylene glycol, hexylene glycol, 1,3-propanediol and 1,5-pentanediol.

The polyol is preferably selected from among glycerol and glycols and is more preferably glycerol.

In terms of the feeling of use and the preservation stability, the amount of the component (F) is in a range of 0.001% by mass to 40% by mass, is preferably in a range of 0.01% by mass to 20% by mass, and is more preferably in a range of 0.1% by mass to 15% by mass, relative to the total mass of the composition.

[Component (G): Water]

Water as a component (G) is an essential component to form a D phase and maintain the system in the cleansing composition of the present disclosure. In terms of improving the preservation stability and giving the fresh feeling after the use, the content of the component (G) in the cleansing composition of the present disclosure is in a range of 0.001% by mass to 25% by mass, is preferably in a range of 0.01% by mass to 20% by mass and is more preferably in a range of 0.1% by mass to 15% by mass.

[Other Arbitrary Components]

The cleansing composition of the present disclosure may further include generally-used other components that are mixed appropriately for various purposes, in addition to the respective components described above. For example, the cleansing composition may include phenoxyethanol as a preservative and tocophenol as an antioxidant. Other mixable components include, for example, a chelating agent, a moisturizing agent, whitening agent, a blood circulation promotor, an anti-inflammatory agent, a germicidal agent, an ultraviolet absorber, a texture improver, a coloring agent, a perfume material, and animal and vegetable extracts.

[Mixing Ratio]

In general, surfactants having relatively high HLB values (for example, HLB of 11 to 15) are easily rinsed off in the process of water washing and are suitable for the cleansing agent. This is because these surfactants have high water solubility and have high ability of emulsifying oil in water. For example, with a view to improving the rinse-off ability of the composition disclosed in Patent Literature 2 described above, the inventors used the surfactants having relatively high HLB values in combination, but all these surfactant mixtures had unstable formulations.

The inventors have made an intensive study to improve the rinse-off ability. The inventors have also made examination of the inventors' fundamental composition by using another type of the surfactant, polyoxyethylene glyceryl fatty acid esters. For example, in an experiment using PEG-8 stearate (HLB 11), instead of the surfactant of the component (C) shown in Patent Literature 2 described above, for the purpose of improving the rinse-off ability, the formulation was unstable. In an experiment using a mixture of an identical type of surfactants having different HLB values, the formulation was stable but did not give the phase inversion feeling.

The inventors have then made examination using mixtures of different types of surfactants. For example, in an experiment using a mixture of PEG-100 stearate (HLB 18.8) and glyceryl stearate (HLB 3.2), the formulation was stable but did not give the phase inversion feeling.

The inventors have further made a wide range of intensive study to improve the feeling of oil film persistence of the dried skin after the rinse-off (the stickiness after use) and have found that an extremely small content of the diester or the triester made the user feel the oil film persistence (stickiness) after the rinse-off. As a result of the intensive study, the inventors have found that using (C) at least one type of polyglycerol fatty acid diester or polyglycerol fatty acid triester having an HLB value of not greater than 13 and (D) at least one type of polyglycerol fatty acid monoester having an HLB value of not smaller than 11 at a designed ratio, in place of the surfactant of the component (C) shown in Patent Literature 2 described above, provides the composition that significantly improves the quality and the performance of the cleansing cosmetic preparation, that has the formulation of temporal stability, and that meets both the satisfactory phase inversion feeling and the non-sticky feeling of the skin after the rinse-off.

The inventors have also found that a ratio (C)/(D) of the mass of the component (C) to the mass of the component (D) (i.e., a mass ratio of the monoester to the diester or the triester) in a range of 0.1 to 10 optimizes an important physical property, the viscosity, for the cleansing cosmetic preparations and has the satisfactory phase inversion feeling, no dripping, and the optimum cleansing effect, the optimum fresh feeling after the rinse-off, and the optimum temporal stability and have achieved the present disclosure. The inventors have further found that a ratio ((C)+(D))/(A) of the total mass of the component (C) and the component (D) to the mass of the component (A) is 0.02 to 4 and is preferably 0.1 to 2. As clearly understood from the foregoing, the inventors have not mixed polyglycerol fatty acid esters of different HLB values that are known in the field of cleansing cosmetic preparations for the purpose of simply adjusting the HLB value. The inventors have found an excellent cleansing cosmetic preparation is prepared by especially mixing the polyglycerol fatty acid diester or the polyglycerol fatty acid triester of the component (C) and the polyglycerol fatty acid monoester of the component (D) at the above ratio.

More specifically, the inventors have found the ratio of the mass of the component (E) to the total mass of the component (C) and the component (D) to eliminate the feeling of oil film persistence even in the case where a large amount of the oil of the component (E) that is not solid at ordinary temperature is added to the cleansing cosmetic preparation (cleansing composition) using the polyglycerol fatty acid esters, the oil, the water content, and the polyol for the purpose of enhancing the phase inversion feeling and the cleansing power. The inventors have found that the mass ratio (E)/((C)+(D)) in a range of 4 to 4000 or more preferably in a range of 10 to 100 achieves the cleansing power as the cleansing cosmetic preparation as well as the satisfactory phase inversion feeling and the non-sticky feeling of the skin after the rinse-off.

[Manufacturing Process]

The cleansing composition of the present disclosure is manufactured by appropriately mixing predetermined components and is manufactured by homogeneously mixing and dispersing all the components irrespective of the sequence of mixing. More specifically, examples described below were obtained by heating the respective components shown in a field "I" and a field "II" to 75 degrees centigrade, stirring the component in the field "I" to form a D phase, gradually adding the components in the field "II" to the D phase with stirring and cooling down the mixture with stirring. The numerical values showing the amounts of the respective components are all based on "% by mass" of the active ingredients.

EXAMPLES

The present disclosure is described in detail with reference to examples, although the present disclosure is not at all limited to these examples. Methods of tests performed in the examples and in comparative examples are described below.

<Results of Evaluation Test 1>

|   |   | Example 1 | Example 2 | Comparative Example 1 | Comparative Example 2 | Comparative Example 3 | Comparative Example 4 | Comparative Example 5 |
|---|---|---|---|---|---|---|---|---|
| I | (A) sucrose laurate | 0.8 | 0.8 | 0.8 | 0.8 | 0.8 | 0.8 | 0.8 |
|   | (A) sucrose palmitate | 0.8 | 0.8 | 0.8 | 0.8 | 0.8 | 0.8 | 0.8 |
|   | (C) polyglyceryl-6 dicaprate (HLB10.2) | 0.9 | 0.74 | — | 0.9 | 1.08 | — | — |
|   | (D) polyglyceryl-10 laurate (HLB15.5) | 0.18 | 0.46 | — | 0.18 | — | 1.08 | — |
|   | (B) sodium stearoyl methyltaurine | 0.2 | 0.2 | — | — | 0.2 | 0.2 | 0.2 |
|   | (F) glycerin | 8 | 8 | 8 | 8 | 8 | 8 | 8 |
|   | hydrogenated starch hydrolysate | 4.2 | 4.2 | 4.2 | 4.2 | 4.2 | 4.2 | 4.2 |
|   | phenoxyethanol | 0.3 | 0.3 | 0.3 | 0.3 | 0.3 | 0.3 | 0.3 |
|   | (G) water | 6 | 6 | 6 | 6 | 6 | 6 | 6 |
| II | (E) ethyl hexyl palmitate | QS 100 | QS 100 | QS 100 | QS 100 | QS 100 | QS 100 | QS 100 |
|   | (E) dicaprylyl ether | 6.4 | 6.4 | 6.4 | 6.4 | 6.4 | 6.4 | 6.4 |
|   | (E) isopropyl myristate | 6 | 6 | 6 | 6 | 6 | 6 | 6 |
|   | tocophenol | 0.1 | 0.1 | 0.1 | 0.1 | 0.1 | 0.1 | 0.1 |

-continued

|  | Example 1 | Example 2 | Comparative Example 1 | Comparative Example 2 | Comparative Example 3 | Comparative Example 4 | Comparative Example 5 |
|---|---|---|---|---|---|---|---|
| Cleansing Effect 1 (Foundation) | ○ | ○ | Δ | ○ | ○ | Δ | Δ |
| Cleansing Effect 2 (Mascara) | ○ | ○ | Δ | ○ | ○ | Δ | Δ |
| Phase Inversion Feeling | ○ | ○ | ○ | ○ | ○ | x | ○ |
| Easy Rinse-Off | ○ | ○ | x | ○ | x | ○ | x |
| Preservation Stability | ○ | ○ | x | x | Δ | ○ | ○ |
| No Feeling of Oil Film Persistence | ○ | ○ | x | ○ | ○ | Δ | x |

<Results of Evaluation Test 3>

|  |  | Example 3 | Comparative Example 11 | Example 4 | Example 5 | Comparative Example 12 | Comparative Example 13 |
|---|---|---|---|---|---|---|---|
| I | (A) sucrose laurate | 0.8 | 0.8 | — | 0.8 | 0.8 | 0.8 |
|  | (A) sucrose palmitate | 0.8 | 0.8 | 3 | 0.8 | 0.8 | 0.8 |
|  | (C) polyglyceryl-6 dicaprate (HLB10.2) | 0.54 | 0.02 | 1.5 | — |  |  |
|  | (C) polyglyceryl-10 dimyristate (HLB12.3) |  |  |  | 0.1 | 1.06 | 0.01 |
|  | (D) polyglyceryl-10 laurate (HLB15.5) | — | — | 0.3 | — | — | — |
|  | (D) polyglyceryl-4 laurate (HLB11.0) | 1.06 | 1.06 | — | 0.98 | 0.02 | 0.01 |
|  | PEG-8 stearate (HLB11.0) |  |  |  |  |  |  |
|  | glyceryl stearate (HLB4.0) |  |  |  |  |  |  |
|  | PEG-100 stearate (HLB18.8) |  |  |  |  |  |  |
|  | PEG-20 glyceryl isostearate (HLB7.0) |  |  |  |  |  |  |
|  | (B) sodium stearoyl methyltaurine | 0.2 | 0.2 | 0.2 | 0.2 | 0.2 | 0.2 |
|  | (F) glycerin | 8 | 8 | 8 | 8 | 8 | 8 |
|  | hydrogenated starch hydrolysate | 4.2 | 4.2 | 4.2 | 4.2 | 4.2 | 4.2 |
|  | phenoxyethanol | 0.3 | 0.3 | 0.3 | 0.3 | 0.3 | 0.3 |
|  | (G) water | 6 | 6 | 6 | 6 | 6 | 6 |
| II | (E) ethyl hexyl palmitate | QS 100 | QS 100 | QS 100 | QS 100 | QS 100 | QS 100 |
|  | (E) dicaprylyl ether | 6.4 | 6.4 | 6.4 | 6.4 | 6.4 | 6.4 |
|  | (E) isopropyl myristate | 6 | 6 | 6 | 6 | 6 | 6 |
|  | tocophenol | 0.1 | 0.1 | 0.1 | 0.1 | 0.1 | 0.1 |
|  | Cleansing Effect 1 (Foundation) | ○ | ○ | ○ | ○ | Δ | Δ |
|  | Cleansing Effect 2 (Mascara) | ○ | Δ | ○ | ○ | ○ | ○ |
|  | Phase Inversion Feeling | ○ | ○ | ○ | ○ | ○ | ○ |
|  | Easy Rinse-Off | ○ | ○ | ○ | ○ | x | x |
|  | Preservation Stability | ○ | ○ | ○ | ○ | ○ | ○ |
|  | No Feeling of Oil Film Persistence | ○ | x | ○ | ○ | ○ | x |

|  |  | Comparative Example 6 | Comparative Example 7 | Comparative Example 8 | Comparative Example 9 | Comparative Example 10 |
|---|---|---|---|---|---|---|
|  | (A) sucrose laurate | 0.8 | 0.8 | 0.8 | 0.8 | 0.8 |
|  | (A) sucrose palmitate | 0.8 | 0.8 | 0.8 | 0.8 | 0.8 |
|  | (C) polyglyceryl-6 dicaprate (HLB10.2) | — | 5.5 | 0.02 | — | — |
|  | (C) polyglyceryl-10 dimyristate (HLB12.3) |  |  |  |  |  |
|  | (D) polyglyceryl-10 laurate (HLB15.5) | — | 1.1 | — | — | 0.18 |
|  | (D) polyglyceryl-4 laurate (HLB11.0) | 1.08 |  |  |  |  |
|  | PEG-8 stearate (HLB11.0) |  |  | 1.06 |  |  |
| I | glyceryl stearate (HLB4.0) |  |  |  | 0.54 |  |
|  | PEG-100 stearate (HLB18.8) |  |  |  | 0.54 |  |
|  | PEG-20 glyceryl isostearate (HLB7.0) |  |  |  |  | 0.9 |
|  | (B) sodium stearoyl methyltaurine | 0.2 | 0.2 | 0.2 | 0.2 | 0.2 |
|  | (F) glycerin | 8 | 8 | 8 | 8 | 8 |
|  | hydrogenated starch hydrolysate | 4.2 | 4.2 | 4.2 | 4.2 | 4.2 |
|  | phenoxyethanol | 0.3 | 0.3 | 0.3 | 0.3 | 0.3 |
|  | (G) water | 6 | 6 | 6 | 6 | 6 |
|  | (E) ethyl hexyl palmitate | QS 100 | QS 100 | QS 100 | QS 100 | QS 100 |
|  | (E) dicaprylyl ether | 6.4 | 6.4 | 6.4 | 6.4 | 6.4 |

|     |                                      |       |       |       |       |       |
| --- | ------------------------------------ | ----- | ----- | ----- | ----- | ----- |
| II  | (E) isopropyl myristate              | 6     | 6     | 6     | 6     | 6     |
|     | tocophenol                           | 0.1   | 0.1   | 0.1   | 0.1   | 0.1   |
|     | Cleansing Effect 1 (Foundation)      | ○     | ○     | ○     | Δ     | ○     |
|     | Cleansing Effect 2 (Mascara)         | Δ     | ○     | ○     | Δ     | ○     |
|     | Phase Inversion Feeling              | Δ     | x     | ○     | Δ     | ○     |
|     | Easy Rinse-Off                       | ○     | ○     | ○     | x     | Δ     |
|     | Preservation Stability               | ○     | x     | x     | ○     | x     |
|     | No Feeling of Oil Film Persistence   | x     | ○     | x     | Δ     | Δ     |

|     |                                       | Example 6  | Example 7  | Comparative Example 14 | Comparative Example 15 |
| --- | ------------------------------------- | ---------- | ---------- | ---------------------- | ---------------------- |
| I   | (A) sucrose laurate                   | 0.8        |            |                        |                        |
|     | (A) sucrose palmitate                 | 0.8        | 3          |                        | 3                      |
|     | (C) polyglyceryl-6 dicaprate (HLB10.2) |           | 2.5        | 2.5                    | 2.5                    |
|     | (C) polyglyceryl-10 dimyristate (HLB12.3) |        |            |                        |                        |
|     | (C) polyglyceryl-10 trilaurate (HLB10.4) | 0.68    |            |                        |                        |
|     | (D) polyglyceryl-10 laurate (HLB15.5) | 0.54       |            |                        |                        |
|     | (D) polyglyceryl-4 laurate (HLB11.0)  |            | 2          | 2                      | 2                      |
|     | (B) sodium stearoyl methyltaurine     | 0.2        | 0.4        | 0.4                    | 0.4                    |
|     | (F) glycerin                          | 8          | 12         | 12                     | 12                     |
|     | hydrogenated starch hydrolysate       | 4.2        | 4.2        | 4.2                    | 4.2                    |
|     | phenoxyethanol                        | 0.3        | 0.3        | 0.3                    | 0.3                    |
|     | (G) water                             | 6          | 8          | 8                      | 58                     |
| II  | (E) ethyl hexyl palmitate             | QS 100 (65.96) | QS 100 (55.1) | QS 100 (58.1)    | QS 100 (5.1)           |
|     | (E) dicaprylyl ether                  | 6.4        | 6.4        | 6.4                    | 6.4                    |
|     | (E) isopropyl myristate               | 6          | 6          | 6                      | 6                      |
|     | tocophenol                            | 0.1        | 0.1        | 0.1                    | 0.1                    |
| Cleansing Effect 1 (Foundation)       |                                      | ○          | ○          | ○                      | Δ                      |
| Cleansing Effect 2 (Mascara)          |                                      | ○          | ○          | ○                      | x                      |
| Phase Inversion Feeling               |                                      | ○          | ○          | ○                      | ○                      |
| Easy Rinse-Off                        |                                      | ○          | ○          | x                      | ○                      |
| Preservation Stability                |                                      | ○          | ○          | x                      | x                      |
| No Feeling of Oil Film Persistence    |                                      | ○          | ○          | x                      | ○                      |

(Note 1) polyglyceryl-6 dicaprate (HLB 10.2): 'SUNSOFT Q-102H-C' (manufactured by Taiyo Kagaku Co., Ltd.)

(Note 2) polyglyceryl-10 dimyristate (HLB 12.3): 'SUNSOFT Q-142Y-C' (manufactured by Taiyo Kagaku Co., Ltd.)

(Note 3) polyglyceryl-10 laurate (HLB 15.5): 'SUNSOFT M-12J' (manufactured by Taiyo Kagaku Co., Ltd.) or 'DERMOFEEL G 10L' (manufactured by Evonik Industries)

(Note 4) polyglyceryl-4 laurate (HLB 11.0): 'TEGO CARE PL4' (manufactured by Evonik Industries)

(Note 5) PEG-8 stearate (HLB 11.0): 'CITHROL 4MS' (manufactured by Croda International plc)

(Note 6) glyceryl stearate (HLB 4.0): 'CUTINA GMS V' (manufactured by Cognis)

(Note 7) PEG-100 stearate (HLB 18.8): 'MYRJ 59 P' (manufactured by Croda International plc)

(Note 8) PEG-20 glyceryl isostearate: 'EMALEX GWIS-320EX' (manufactured by Nihon Emulsion Co., Ltd.)

(Note 9) polyglyceryl-10 trilaurate (HLB 10.4) 'SUNSOFT Q-123Y-C' (manufactured by Taiyo Kagaku Co., Ltd.)

Especially, compared with the examples of the cleansing composition according to the present disclosure, Comparative Example 11 shows the result in the case of having a significantly low ratio of the polyglycerol fatty acid diester of the component (C) to the polyglycerol fatty acid monoester of the compound (D); Comparative Example 12 shows the result in the case of having a significantly low ratio of the polyglycerol fatty acid monoester of the component (D) to the polyglycerol fatty acid diester of the component (C); Comparative Example 13 shows the result in the case of having small amounts of both the component (C) and the component (D); Comparative Example 14 shows the result in the case of not using the sugar ester of the fatty acid of the component (A); and Comparative Example 15 shows the result in the case of decreasing the amount of the oil of the component (E) and increasing the content of water of the component (G).

[Evaluation of Cleansing Effect 1]

After a foundation of the following formulation was applied in layers on the skin and was left for two hours, the face was cleansed with a cleansing cosmetic preparation of each of the examples and the comparative examples. The effect of removing the cosmetic after the cleansing was evaluated by five members of a panel. The evaluation criteria are given below:

open circle: not less than four members out of the five members approved the high effect of removal of the foundation;

open triangle: not less than two members but less than four members out of the five members approved the high effect of removal of the foundation; and cross mark: less than two members out of the five members approved the high effect of removal of the foundation.

| Formulation of Foundation | (% by mass) |
|---|---|
| (1) decamethylcyclopentasiloxane | 14.0 |
| (2) octamethylcyclotetrasiloxane | 24.0 |
| (3) siliconed pullulan | 15.0 |
| (4) isostearic acid | 1.0 |
| (5) titanium oxide | 5.0 |
| (6) octyl methoxycinnamate | 5.0 |
| (7) dextrin fatty acid covered powder | 25.0 |
| (8) alcohol | rest |

[Evaluation of Cleansing Effect 2]

After a mascara (waterproof type) was applied on the eyelashes and was left for two hours, the applied part of the eyes was cleansed with a cleansing cosmetic preparation of each of the examples and the comparative examples by a procedure of applying the cleansing cosmetic preparation in circular shapes thirty times, adding a slight amount of water to emulsify the cleansing cosmetic preparation and washing out the mascara and the cleansing cosmetic preparation with tap water. The results of visual observation of removal of the mascara were evaluated according to the following evaluation criteria:

open circle: not lower than 80 percent of the mascara was removed;

open triangle: not higher than 50 percent but lower than 80 percent of the mascara was removed; and cross mark: lower than 50 percent of the mascara was removed.

[Evaluation of Phase Inversion Feeling]

Each of the five members of the panel applied 0.1 g of each of the compositions on the back of the hand in a circular shape. Each member made an evaluation by counting the number of rubbing actions required to change the texture. The average number of rubbing actions was classified into the following three categories:

open circle: less than 15 times;

open triangle: 15 to 30 times; and cross mark: more than 30 times.

[Evaluation of Easy Rinse-Off]

Each of the five members of the panel applied 0.1 g of each of the cleansing compositions on the back of the hand in circular shapes fifteen times to spread the cleansing composition, added a slight amount of water to emulsify the cleansing composition, rinsed the hand with tap water (the flow rate of rinsing water: 1000 mL/minute, water temperature: 25 to 30° C.) for 15 seconds, and evaluated the sliminess of the hand after 15 seconds of rinsing. The evaluation criteria are given below:

open circle: not less than four members out of the five members approved the easy rinse-off;

open triangle: not less than two members but less than four members out of the five members approved the easy rinse-off; and cross mark: less than two members out of the five members approved the easy rinse-off.

[Evaluation of Preservation Stability]

Each cleansing composition was filled in a transparent glass vial and was kept under a temperature condition of 50° C. for one month. The state of the cleansing composition in each vial was checked for any changes (in the color, the smell, pH, the viscosity and the state of emulsion) and was evaluated according to the following criteria:

open circle: no change open triangle: no separation with slight changes cross mark: separation

[Evaluation of No Feeling of Oil Film Persistence]

After the evaluation of the cleansing effect, each of the five members of the panel evaluated no feeling of oil film persistence on the dry skin after the cleansing according to the following evaluation criteria:

open circle: not less than four members out of the five members approved no feeling of oil film persistence;

open triangle: not less than two members but less than four members out of the five members approved no feeling of oil film persistence; and cross mark: less than two members out of the five members approved no feeling of oil film persistence.

As clearly shown by the examples in Table 1 and Table 2 given above, the cleansing composition of the present disclosure (emulsion-type cleansing cosmetic preparation by applying D phase emulsification) has excellent performances in all the conditions of the cleaning effect, the phase inversion feeling (the spread in the course of application and the high speed spread over the makeup), the easy rinse-off, no feeling of oil film persistence and the preservation stability.

As shown by Comparative Examples 1, 3, 4, 5 and 6 in Table 1, on the other hand, the lack of at least one of the component (C) and the component (D) does not meet all the conditions of the cleaning effect, the phase inversion feeling, the easy rinse-off, no feeling of oil film persistence and the preservation stability. As shown by Comparative Example 2 in Table 1, the lack of the component (B) results in the poor preservation stability.

Additionally, as shown by Comparative Examples 8 to 10 in Table 2, mixing another surface active agent in place of the component (C) or the component (D) fails to provide a cleansing composition that satisfies all of the cleaning effect, the phase inversion feeling, the easy rinse-off, no feeling of oil film persistence and the preservation stability and fails to achieve the object of the present disclosure.

Furthermore, as shown by Comparative Examples 11 and 12 in Table 2, the ratio of the mass of the component (C) to the mass of the component (D) out of the range of 0.1 to 10 causes problems of, for example, the easiness of rinse-off and the oil film persistence. As shown by Comparative Example 14 in Table 3, the lack of the component (A) causes problems of the easiness of rinse-off, the preservation stability and the oil film persistence. Additionally, as shown by Comparative Example 15 in Table 3, a small content of the oil of the component (E), a large content of water of the component (G) and the ratio of the mass of the component (E) to the total mass of the component (C) and the component (D) out of the range of 10 to 100 causes problems of the cleansing effect and the preservation stability. Moreover, as shown by Comparative Examples 7 and 13, the ratio of the total mass of the component (C) and the component (D) to the mass of the component (A) out of the range of 0.02 to 4.0 causes problems of the phase inversion feeling, the preservation stability, the easiness of rinse-off, and the oil film persistence.

As described above, the cleansing composition according to the embodiment of the present disclosure comprises (A) a sugar ester of a fatty acid; (B) at least one type of an anionic surfactant selected from among amino acid surfactants and taurine surfactants; (C) at least one type of a polyglycerol fatty acid diester or a polyglycerol fatty acid triester having an HLB value of not greater than 13; (D) at least one type of a polyglycerol fatty acid monoester having an HLB value of not smaller than 11; (E) an oil that has a liquid form or a paste (non-solid) form at ordinary temperature; (F) a polyol; and (G) water. More preferably, the component (C) has the HLB value of 7 to 13, and the component (D) has the HLB value of 11 to 16. More preferably, the ratio (C)/(D) of the mass of the component (C) to the mass of the component (D) is 0.1 to 10. More preferably, the ratio ((C)+(D))/(A) of the total mass of the component (C) and the component (D) to the mass of the component (A) is 0.02 to 4. More preferably, the ratio (E)/((C)+(D)) of the mass of the component (B) to the total mass of the component (C) and the component (D) is 10 to 100.

In the cleansing cosmetic preparation, increasing the content of the oil component generally gives a significant problem of the feeling of oil film persistence (stickiness) after the rinse-off. The present disclosure has the optimum combination of the polyglycerol fatty acid esters, the combinations and the ratios of the oil and the other effective surfactants to the polyglycerol fatty acid esters by examining, with the originality and the ingenuity, the conditions of the cleansing cosmetic preparation using the polyglycerol fatty acid esters, the oil, water and the polyol. As a result, the cleansing composition according to the embodiment of the present disclosure uses the polyglycerol fatty acid esters, a large amount of the oil, water and the polyol, but has the excellent cleansing effect, the phase inversion feeling, achieves the easy rinse-off in the course of water washing, suppresses the feeling of oil film persistence of the skin after the use, and has the excellent preservation stability. The cleansing composition according to the embodiment of the present disclosure is preferably applied as a skin cleansing cosmetic preparation and is preferably usable to be directly (without foaming) applied on any of the face, the body, the limbs, the hair and the like, to be rubbed to spread over the spot and to be wiped out or washed out.

The present disclosure is not limited to the configuration of the embodiment described above but may be modified, altered or changed in any of various ways within the scope of the present disclosure. The cleansing composition of the present disclosure preferably has a cream form or a gel form, because of the convenience and the more distinct feeling of a change to a liquid form by phase inversion.

The invention claimed is:

1. A cleansing composition comprising:
    (A) a sugar ester of a fatty acid;
    (B) at least one anionic surfactant selected from the group consisting of amino acid surfactants and taurine surfactants;
    (C) at least one polyglycerol fatty acid diester or a polyglycerol fatty acid triester having an HLB value of not greater than 13;
    (D) at least one polyglycerol fatty acid monoester having an HLB value of not smaller than 11;
    (E) an oil that has a liquid form or a paste (non-solid) form at ordinary temperature;
    (F) a polyol; and
    (G) water, wherein:
    i) a ratio by mass of E:(C+D) is 10 to 100;
    ii) a ratio by mass of C:D is 0.1 to 10; and
    iii) a ratio by mass of (C+D):A is 0.02 to 4.

2. The cleansing composition according to claim 1, wherein the component (E) is in a range of 40% by mass to 90% by mass relative to a total mass of the cleansing composition.

3. The cleansing composition according to claim 1, wherein the component (C) preferably has the HLB value of 7 to 13, and the component (D) has the HLB value of 11 to 16.

4. The cleansing composition according to claim 1, wherein the component (C) is polyglyceryl-6 dicaprate, and the component (D) is polyglyceryl-10 laurate.

5. The cleansing composition according to claim 1, wherein the component (C) is at least one selected from the group consisting of polyglyceryl-6 dicaprate, polyglyceryl-10 dimyristate, polyglyceryl-5 dilaurate, polyglyceryl-10 distearate, polyglyceryl-2 sesquioleate, polyglyceryl-10 dioleate, polyglyceryl-10 distearate, polyglyceryl-10 diisostearate, polyglyceryl-5 dioleate, and polyglyceryl-10 trilaurate.

6. The cleansing composition according to claim 1, wherein the component (D) is at least one selected from the group consisting of polyglyceryl-10 laurate, polyglyceryl-4 laurate, polyglyceryl-6 caprate, polyglyceryl-10 caprate, polyglyceryl-5 myristate, polyglyceryl-5 stearate, polyglyceryl-5 caprate, polyglyceryl-10 myristate, polyglyceryl-10 oleate, polyglyceryl-10 stearate, polyglyceryl-5 laurate, polyglyceryl-5 oleate, polyglyceryl-10 laurate, polyglyceryl-10 myristate, polyglyceryl-10 stearate, polyglyceryl-10 isostearate, and polyglyceryl-6 oleate.

7. The cleansing composition according to claim 1, wherein the component (C) is polyglyceryl-10 trilaurate, and the component (D) is polyglyceryl-10 laurate.

8. The cleansing composition according to claim 1, wherein the ratio by mass of (C+D):A is 0.1 to 2.

9. The cleansing composition according to claim 1, wherein the component (A) is in a range of 0.1% by mass to 5% by mass, the component (B) is in a range of 0.05% by mass to 5% by mass, the component (C) is in a range of 0.01% by mass to 5% by mass, the component (D) is in a range of 0.01% by mass to 5% by mass, the component (E) is in a range of 50% by mass to 85% by mass, the component (F) is in a range of 0.1% by mass to 15% by mass, and the component (G) is in a range of 0.1% by mass to 15% by mass to a total mass of the cleansing composition.

* * * * *